United States Patent
Sigl (10) Patent No.: US 10,568,951 B2
(45) Date of Patent: Feb. 25, 2020

(54) PHARMACEUTICAL COMPOSITION OF AN ANTI-VEGF ANTIBODY

(71) Applicant: FORMYCON AG, Martinsried/Planegg (DE)

(72) Inventor: Rainer Sigl, Landsberg (DE)

(73) Assignee: FORMYCON AG (DE)

( * ) Notice: Subject to any disclaimer, the term of this patent is extended or adjusted under 35 U.S.C. 154(b) by 252 days.

(21) Appl. No.: 15/037,254

(22) PCT Filed: Nov. 13, 2014

(86) PCT No.: PCT/EP2014/074464
§ 371 (c)(1),
(2) Date: May 17, 2016

(87) PCT Pub. No.: WO2015/071348
PCT Pub. Date: May 21, 2015

(65) Prior Publication Data
US 2016/0297877 A1  Oct. 13, 2016

(30) Foreign Application Priority Data
Nov. 18, 2013 (EP) .................................... 13193391

(51) Int. Cl.
*A61K 39/395* (2006.01)
*C07K 16/22* (2006.01)
*A61K 39/00* (2006.01)

(52) U.S. Cl.
CPC ...... *A61K 39/001135* (2018.08); *C07K 16/22* (2013.01); *C07K 2317/24* (2013.01); *C07K 2317/55* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,608,038 A | 3/1997 | Eibl et al. | |
| 6,582,959 B2 | 6/2003 | Kim | |
| 6,703,020 B1 | 3/2004 | Thorpe et al. | |
| 8,372,396 B2 | 2/2013 | Andya et al. | |
| 9,226,961 B2* | 1/2016 | Gokarn | A61K 9/0019 |
| 2003/0190317 A1 | 10/2003 | Baca et al. | |
| 2010/0015158 A1 | 1/2010 | Robinson et al. | |
| 2011/0076273 A1 | 3/2011 | Adler et al. | |
| 2012/0141371 A2* | 6/2012 | Rock | C07K 16/241 424/1.49 |
| 2015/0297740 A1* | 10/2015 | Rau | A61K 47/48215 424/158.1 |

FOREIGN PATENT DOCUMENTS

| | | |
|---|---|---|
| EP | 0 661 060 A2 | 7/1995 |
| EP | 0 666 868 B1 | 4/2002 |
| EP | 1 977 763 A1 | 10/2008 |
| WO | WO 94/10202 A1 | 5/1994 |
| WO | WO 96/30046 A1 | 10/1996 |
| WO | WO 98/45331 A2 | 10/1998 |
| WO | WO 98/45332 A2 | 10/1998 |
| WO | WO 2005/044853 A2 | 5/2005 |
| WO | WO 2007/149334 A2 | 12/2007 |
| WO | WO 2010/060768 A1 | 6/2010 |
| WO | WO 2011/084750 A1 | 7/2011 |

OTHER PUBLICATIONS https://www.powerpak.com/course/print/113227, Compounding Preparations for Ophthalmic Use in Humans, downloaded Oct. 2, 2018.*
Extended European Search Report for European Application No. 13193391.3, European Patent Office, Germany, dated Jan. 27, 2014, 7 pages.
Notification of Transmittal of International Search Report and the Written Opinion of the International Searching Authority, or the Declaration, European Patent Office, Netherlands, dated Jan. 8, 2015, 9 pages.

* cited by examiner

*Primary Examiner* — Christine J Saoud
(74) *Attorney, Agent, or Firm* — Sterne, Kessler, Goldstein & Fox P.L.L.C.

(57) ABSTRACT

The present invention relates to liquid pharmaceutical formulations for intravitreal injection of an anti-VEGF antibody which does not contain saccharides for use in the treatment of age-related macular degeneration.

11 Claims, 3 Drawing Sheets

PHARMACEUTICAL COMPOSITION OF AN ANTI-VEGF ANTIBODY

FIELD OF THE INVENTION

The present invention relates to pharmaceutical compositions of an anti-VEGF antibody which do not contain saccharides.

BACKGROUND OF THE INVENTION

Vascular endothelial growth factor (VEGF) is a signal protein that stimulates vasculogenesis (i.e. de novo formation of new blood vessels) and angiogenesis (i.e. formation of new blood vessels from pre-existing vessels). There are at least six subtypes of VEGF, i.e. VEGF-A, VEGF-B, VEGF-C, VEGF-D, virus VEGF-E and placental VEGF (PlGF). VEGF-A is associated with increases of vascular permeability, degeneration of the extracellular matrix and cell aggravation. Four isomers of VEGF-A that arise from alternative splicing of mRNA have been reported in humans (VEGF121, VEGF165, VEGF184, VEGF206) (Ferrara and Davis Smyth, Endocr Rev, 1997, 18:1-22). VEGF-A binds to receptors VEGFr-1 and VEGFr-2 (Kajdaniuk et al., Endokrynol Pol, 2011, 62(5):444-55; Kajdaniuk et al., Endokrynol Pol, 2011, 62(5):456-64).

The specificity of VEGF action for endothelial cells supports a key role in the process of abnormal blood vessel growth and vascular leakage. Anti-VEGF agents have demonstrated efficacy in reducing corneal neovascularisation in both animal models and clinical trials (Okamoto et al., Am J Pathol, 1997, 151:281-91; Adamis et al., Arch Ophthalmol, 1996, 114:66-71). Specifically, anti-VEGF antibodies have been used for the treatment of treatments of intraocular neovascular disorders.

Currently available anti-VEGF antibodies are bevacizumab and ranibizumab. Bevacizumab is a full-length, humanized murine monoclonal antibody that recognizes all isoforms of VEGF. Ranibizumab is the Fab fragment of the humanized murine monoclonal antibody that is used to create bevacizumab and has been affinity-matured so that it binds VEGF-A with a significantly higher affinity than bevacizumab. Ranibizumab and bevacizumab appear to have similar efficacy profiles in the treatment of neovascular age-related macular degeneration although rare adverse events seem to occur more often with bevacizumab (Johnson and Sharma, Curr Opin Ophthalmol, 2013, 24(3):205-12).

For medical purposes stable antibody compositions are of great interest, in particular ready-to-use solutions which require no dissolution or reconstitution before use. A main problem of such a liquid composition is a decreasing antibody content due to the formation of antibody dimers or insoluble particles during repeated freeze/thaw cycles during manufacturing or antibodies being degraded and forming degradation products during long-term storage.

Many efforts have been made to provide a method for storing antibodies in solutions. Stabilising effects were found by adding polymers including proteins such as human serum albumin or oligomers such as polyols, amino acids, and surfactants as stabilisers for preventing chemical or physical changes. However, the addition of biopolymers such as proteins as stabilisers is inconvenient, as it requires a very complicated step for eliminating contaminants such as viruses and prions.

Moreover, antibody-containing compositions tend to form high-viscosity solutions by molecular interactions. Sugars such as trehalose or sucrose enhance molecular interactions and increase viscosity and the resulting high-viscosity compositions can be difficult to dispense, draw into syringes and inject. Further, the use of a sugar makes a formulation more expensive and the use of sugars which do not naturally occur in mammals may pose a risk for intolerance.

U.S. Pat. No. 8,372,396 B2 describes monoclonal antibody preparations formulated in a saccharide-containing histidine-acetate buffer.

EP 0 661 060 B1 describes stable, highly concentrated intravenously tolerable immunoglobulin preparations.

US 2011/0076273 A1 discloses highly concentrated anti-CD20 antibody formulations comprising a buffering agent, a stabilizer or a mixture of two or more stabilizers, a non-ionic surfactant and optionally a hyaluronidase enzyme.

EP 1 977 763 A1 discloses antibody-containing lyophilized formulations, wherein the formulations substantially consist of an antibody, one or more amino acids, a salt as a buffer, and a surfactant and are free from reducing sugars, non-reducing sugars, sugar alcohols or polysaccharides.

WO 2011/084750 A1 discloses aqueous stable antibody formulations comprising an arginine buffer.

It is an object of the present invention to provide a pharmaceutical composition which is suitable for intravitreal injection and which is stable in liquid form without the addition of excipients such as preservatives or sugars. Preferably such a composition is suitable for the treatment of AMD and formulated in a prefilled syringe. Another object of the present invention is to provide a stable liquid pharmaceutical composition which is formulated such that it does not contain any ingredients which do not naturally occur in humans.

SUMMARY OF THE INVENTION

It was surprisingly found that a liquid composition comprising a buffer, a non-ionic surfactant and an anti-VEGF antibody or antigen-binding fragment thereof and optionally an inorganic salt is stable in the absence of saccharides. Thereby, a cheaper, less viscous and less complex pharmaceutical composition was obtained. Further, the use of sugars such as trehalose which does not naturally occur in mammals was avoided.

A further advantage of the liquid pharmaceutical composition of the present invention is that it does not require a lyophilisation step and thus is thus produced in a shorter time and with reduced costs. Another advantage is that the composition has a pH in the range of 5.0 to 7.0, preferably 5.5 to 6.5, more preferably with pH 5.5 or 6.2, i.e. a pH close to the physiological pH.

Thus, the present invention provides a liquid anti-VEGF antibody composition for intravitreal administration which does not contain saccharides.

The object of the present invention is solved by the subject-matter of the independent claims. Preferred embodiments are apparent from the dependent claims.

Accordingly, in one embodiment the present invention provides a liquid pharmaceutical composition for intravitreal injection comprising a buffer, a non-ionic surfactant, an anti-VEGF antibody or antigen-binding fragment thereof, and, optionally, an inorganic salt, wherein the composition does not contain saccharides.

In a preferred embodiment, the liquid pharmaceutical composition has a pH in the range of 5.0 and 7.0, preferably in the range of 5.5 and 6.2.

In a further preferred embodiment, the buffer in the liquid pharmaceutical composition is Histidine hydrochloride/L-histidine or $Na_2HPO_4/NaH_2PO_4$.

In another preferred embodiment, the buffer is present in a concentration of from 5 mM to 250 mM.

In yet another preferred embodiment, the buffer in the liquid pharmaceutical composition is Histidine hydrochloride/L-histidine in a concentration of 10 mM.

In a further embodiment, the non-ionic surfactant in the liquid pharmaceutical composition is polysorbate 20.

In a further preferred embodiment, the non-ionic surfactant in the pharmaceutical composition has a concentration in the range of 0.002 to 0.02% (w/v).

In another preferred embodiment, the liquid pharmaceutical composition comprises an inorganic salt, preferably NaCl.

In yet a further preferred embodiment, the inorganic salt in the liquid pharmaceutical composition is present in a concentration in the range of 10 to 200 mM, preferably 150 mM.

In a further embodiment, the anti-VEGF antibody or antigen-binding fragment thereof in the liquid pharmaceutical composition is a humanized monoclonal Fab fragment, preferably ranibizumab.

In another preferred embodiment, the liquid pharmaceutical composition consists of Histidine hydrochloride/L-histidine, polysorbate 20, NaCl, water and ranibizumab and has a pH of 5.5 or 6.2.

Most preferably, the liquid pharmaceutical composition consists of 10 mM Histidine hydrochloride/L-histidine, 0.01% (w/v) polysorbate 20, 150 mM NaCl, water and 10 mg/ml ranibizumab and has a pH of 5.5 or 6.2.

In a further preferred embodiment, the liquid pharmaceutical composition of the invention is for use in the treatment of an intraocular neovascular disease, preferably for the treatment of age-related macular degeneration (AMD), the treatment of visual impairment due to diabetic macular oedema (DME), the treatment of visual impairment due to macular oedema secondary to retinal vein occlusion (branch RVO or central RVO), or the treatment of visual impairment due to choroidal neovascularisation (CNV) secondary to pathologic myopia.

In another embodiment, the invention relates to a prefilled syringe containing the liquid pharmaceutical composition of the invention.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF THE INVENTION

The present invention as illustratively described in the following may suitably be practiced in the absence of any element or elements, limitation or limitations, not specifically disclosed herein.

The present invention will be described with respect to particular embodiments, but the invention is not limited thereto, but only by the claims.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. a cell or organism is defined to be obtainable by a specific method, this is also to be understood to disclose a cell or organism which is obtained by this method.

Where an indefinite or definite article is used when referring to a singular noun, e.g. "a", "an" or "the", this includes a plural of that noun unless something else is specifically stated.

The term "pharmaceutical composition" as used herein refers to any composition comprising a chemical substance or active ingredient which composition is intended for use in the medical cure, treatment, or prevention of disease and which is in such a form as to permit the active ingredient to be effective. In particular, a pharmaceutical composition does not contain excipients which are unacceptably toxic to a subject to which the composition is to be administered. The pharmaceutical compositions are sterile, i.e. aseptic and free from all living microorganisms and their spores. The pharmaceutical composition of the present invention is liquid and stable.

In a "liquid composition" the pharmaceutically active agent, e.g. anti-VEGF antibody, can be combined with a variety of excipients to ensure a stable active medication following storage. The liquid pharmaceutical composition of the invention is at no point lyophilised, i.e. the production method does not contain a lyophilisation step and the composition is not lyophilised for storage. Liquid compositions can be stored in vials, IV bags, ampoules, cartridges, and prefilled or ready-to-use syringes.

A "stable" liquid composition is one in which the antibody contained therein essentially retains its physical stability and/or chemical stability and/or biological activity upon storage for a certain period. Preferably, the composition essentially retains upon storage its physical and chemical stability, as well as its biological activity. Various analytical techniques for measuring protein stability are available in the art and are reviewed, for example, in Peptide and Protein Drug Delivery, 247-301, Vincent Lee Ed, Marcel Dekker, Inc, New York, N.Y., Pubs (1991) and Jones, Adv Drug Delivery Rev, 1993, 10:29-90. For example, stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection), by assessing charge heterogeneity using cation exchange chromatography or capillary zone electrophoresis, amino-terminal or carboxy-terminal sequence analysis, mass spectrometric analysis, SDS-PAGE analysis to compare reduced and intact antibody, peptide map (for example tryptic or LYS-C) analysis, evaluating biological activity or antigen binding function of the antibody, etc.

Preferably, the pharmaceutical composition is stable at a temperature of about 40° C. for at least about 2-4 weeks, and/or is stable at a temperature of about 5° C. and/or 15° C. for at least 3 months, and/or is stable at a temperature of about 20° C. for at least 3 months or at least 1 year. Furthermore, the formulation is preferably stable following freezing (to, e.g., −70° C.) and thawing of the formulation, for example following 1, 2, 3 or 4 cycles of freezing and thawing.

For example, in the pharmaceutical composition of the present invention the percentage of antibody polymers as measured by asymmetrical flow field-flow fractionation is not more than 5%, preferably not more than 4.5% or 4%, more preferably not more than 3.5% or 3% and most preferably not more than 2.5% after storage of the composition at 40° C. for 28 days.

A "buffer" is an aqueous solution consisting of a mixture of a weak acid and its conjugate base or vice versa which resists changes in its pH and therefore keeps the pH at a nearly constant value. The buffer of the present invention preferably has a pH in the range from about 5.0 to about 7.0, preferably from about 5.2 to about 6.8, more preferably from about 5.5 to 6.5, even more preferably from about 5.5 to 6.2 and most preferably has a pH of about 5.5 or 6.2. Examples of buffers that will control the pH in this range include acetate, succinate, phosphate, gluconate, histidine, citrate, glycylglycine and other organic or inorganic acid buffers.

Preferably, the buffer is a histidine buffer or a phosphate buffer.

The terms "histidine-containing buffer" and "histidine buffer" are used interchangeably herein and refer to a buffer comprising histidine. Examples of histidine buffers include histidine chloride, histidine hydrochloride, histidine acetate, histidine phosphate, and histidine sulphate. The preferred histidine buffer of the invention further comprises L-histidine. Even more preferably the histidine buffer of the invention comprises histidine hydrochloride, most preferably it comprises histidine hydrochloride and L-histidine. Preferably, the histidine buffer or histidine hydrochloride buffer or histidine hydrochloride/L-histidine buffer has a pH in the range from about 5.0 to about 7.0, preferably from about 5.2 to about 6.8, more preferably from about 5.5 to 6.5, even more preferably from about 5.5 to 6.2 and most preferably has a pH of about 5.5 or 6.2.

The phosphate buffer consists of a mixture of monobasic dihydrogen phosphate and dibasic monohydrogen phosphate. Preferably, the phosphate buffer is a sodium phosphate buffer consisting of sodium dihydrogen phosphate and disodium monohydrogen phosphate or a potassium phosphate buffer consisting of potassium dihydrogen phosphate and dipotassium monohydrogen phosphate. More preferably, it is a sodium phosphate buffer consisting of sodium dihydrogen phosphate and disodium monohydrogen phosphate. Preferably, the phosphate buffer or sodium phosphate buffer has a pH in the range from about 5.0 to about 7.0, preferably from about 5.2 to about 6.8, more preferably from about 5.5 to 6.5, even more preferably from about 5.5 to 6.2 and most preferably has a pH of about 5.5 or 6.2. The concentration of the histidine or phosphate buffer is preferably in the range of 5 to 250 mM, 5 to 200 mM or 6 to 150 mM, more preferably in the range of 7 to 120 mM, 8 to 100 mM, 9 to 70 mM, 10 to 50 mM, 10 to 40 mM, or 5 to 10 mM, even more preferably the buffer has a concentration of 240 mM, 220 mM, 185 mM, or 10 mM, and most preferably 10 mM.

The concentration of the buffer in the pharmaceutical composition depends on the presence of an inorganic salt, such as NaCl, since the inorganic salt contributes to the tonicity of the pharmaceutical composition so that in a liquid pharmaceutical composition which does not contain an inorganic salt the buffer concentration has to be higher to reach isotonicity. In the absence of an inorganic salt the buffer has a concentration in the range of 150 to 250 mM, preferably of 185 to 240 mM, more preferably the buffer has a concentration of 185 mM, 220 mM, or 240 mM.

In a further embodiment, the concentration of the buffer in the liquid pharmaceutical composition in the absence of an inorganic salt is in the range of 185 to 240 mM with a pH in the range of 5.0 to 7.0, preferably in the range of 5.5 to 6.5, more preferably in the range of 5.5 to 6.2, even more preferably 185 to 240 mM with a pH of 5.5, 185 to 240 mM with a pH of 6.2, or 185 to 240 mM with a pH of 6.5, and most preferably the buffer as a concentration of 185 mM with a pH of 5.5, 220 mM with pH 6.2 or 240 mM with a pH of 6.5.

In a further embodiment the buffer of the liquid pharmaceutical composition in the presence of an inorganic salt, such as NaCl, has a concentration in the range of 5 to 50 mM with a pH in the range of 5.0 to 7.0, preferably in the range of 5.5 to 6.5, more preferably in the range of 5.5 to 6.2, yet more preferably the buffer has a concentration in the range of 5 to 20 mM with a pH of 5.5, 5 to 20 mM with a pH of 6.2, or 5 to 20 mM with a pH of 6.5, even more preferably the buffer as a concentration of 10 mM with a pH of 5.5, 10 mM with a pH of 6.2 or 10 mM with a pH of 6.5, wherein the buffer is $Na_2HPO_4/NaH_2PO_4$ or histidine hydrochloride/L-histidine. In the most preferred embodiment the buffer of the liquid pharmaceutical composition in the presence of an inorganic salt, such as NaCl, is a histidine hydrochloride/L-histidine buffer with a concentration of 10 mM and a pH of 5.5, a histidine hydrochloride/L-histidine buffer with a concentration of 10 mM and a pH of 6.2, a $Na_2HPO_4/NaH_2PO_4$ buffer with a concentration of 10 mM and a pH of 6.2, or a $Na_2HPO_4/NaH_2PO_4$ buffer with a concentration of 10 mM and a pH of 6.5. Further preferred is that the inorganic salt is NaCl with a concentration of 150 mM and the buffer.

In a particular preferred embodiment, the buffer is a histidine-containing buffer comprising histidine hydrochloride/L-histidine in a concentration in the range of 5 to 250 mM, more preferably in the range of 5 to 200, 5 to 150, 5 to 100, 5 to 50 mM, 5 to 40 mM, 5 to 30 mM, 5 to 20 mM, or 5 to 10 mM, even more preferably histidine hydrochloride/L-histidine has a concentration of 240 mM, 220 mM, 185 mM, 100 mM, 50 mM, 20 mM, or 10 mM, and most preferably 10 mM.

In another particular preferred embodiment the buffer is histidine hydrochloride/L-histidine with a concentration of 10 mM.

The pharmaceutical compositions of the present invention comprising a histidine buffer are preferably prepared by dissolving L-histidine, L-histidine-HCl and the inorganic salt, preferably sodium chloride, in water before adding the non-ionic surfactant, preferably polysorbate 20 and then adding the anti-VEGF antibody or antigen-binding fragment thereof. The pharmaceutical compositions of the present invention comprising a phosphate buffer are preferably prepared by dissolving disodium hydrogen phosphate and sodium dihydrogen phosphate in water before adding the inorganic salt, preferably sodium chloride, and the non-ionic surfactant, preferably polysorbate 20. Finally, the anti-VEGF antibody or antigen-binding fragment thereof is added.

A "surfactant" as used herein refers to an amphiphilic compound, i.e. a compound containing both hydrophobic groups and hydrophilic groups which lowers the surface tension (or interfacial tension) between two liquids or between a liquid and a solid. A "non-ionic surfactant" has no charged groups in its head. The formation of insoluble particles during freeze/thaw cycles of antibody-containing compositions can be remarkably inhibited by addition of surfactants. Examples of "non-ionic surfactants" include e.g. polyoxyethylene glycol alkyl ethers, such as octaethylene glycol monododecyl ether, pentaethylene glycol monododecyl ether; polyoxypropylene glycol alkyl ethers; glucoside alkyl ethers, such as decyl glucoside, lauryl glucoside, octyl glucoside; polyoxyethylene glycol octylphenol ethers, such as triton X-100; polyoxyethylene glycol alkylphenol ethers, such as nonoxynol-9; glycerol alkyl esters, such as glyceryl laurate; polyoxyethylene glycol sorbitan alkyl esters, such as polysorbate; sorbitan alkyl esters, such as spans; cocamide MEA, cocamide DEA, dodecyldimethylamine oxide; block copolymers of polyethylene glycol and polypropylene glycol, such as poloxamers; and polyethoxylated tallow amine (POEA). The pharmaceutical compositions of the present invention can contain one or more of these surfactants in combination.

Preferred non-ionic surfactants for use in the pharmaceutical compositions of the present invention are polysorbates such as polysorbate 20, 40, 60 or 80, and especially polysorbate 20 (e.g. Tween 20).

The concentration of the non-ionic surfactant is in the range of 0.005 to 0.02% (w/v), preferably in the range of 0.007 to 0.018% (w/v) or 0.008 to 0.015% (w/v), more preferably in the range of 0.009 to 0.012% (w/v), or 0.009 to 0.011% (w/v), and most preferably it is 0.01% (w/v), relative to the total volume of the composition.

In a preferred embodiment, the non-ionic surfactant is polysorbate 20 with a concentration in the range of 0.005 to 0.02% (w/v), preferably in the range of 0.007 to 0.018% (w/v) or 0.008 to 0.015% (w/v), more preferably in the range of 0.009 to 0.012% (w/v), or 0.009 to 0.011% (w/v), and most preferably it is 0.01% (w/v), relative to the total volume of the composition.

In a particularly preferred embodiment the non-ionic surfactant is polysorbate 20 with a concentration of 0.01% (w/v), relative to the total volume of the composition.

Herein, an "inorganic salt" refers to an ionic compound which has osmoregulatory properties. An inorganic salt such as sodium chloride (NaCl) can dissociate in solution into its constituent ions, i.e. NaCl dissociates into $Na^+$ and $Cl^-$ ions, which both affect the osmotic pressure, i.e. the osmolality, of the solution. Preferred inorganic salts for use in the pharmaceutical formulation of the present invention are potassium chloride, calcium chloride, sodium chloride, sodium phosphate, potassium phosphate and sodium bicarbonate. Preferably the inorganic salt is a sodium salt, more preferably it is sodium chloride (NaCl).

The concentration of the inorganic salt in the pharmaceutical composition of the present invention is preferably in the range of 10 to 200 mM, more preferably in the range of 20 to 190 mM, 30 to 180 mM, 50 to 170 mM, 70 to 160 mM, or 80 to 150 mM, even more preferably the inorganic salt has a concentration in the range of 90 to 150 mM, 100 to 150 mM, 120 to 150 mM, 150 to 180 or 150 to 170 mM, and most preferably the concentration is 150 mM.

In a particular preferred embodiment, the inorganic salt is NaCl with a concentration in the range of 10 to 200 mM, more preferably in the range of 20 to 190 mM, 30 to 180 mM, 50 to 170 mM, 70 to 160 mM, or 80 to 150 mM, even more preferably the inorganic salt has a concentration in the range of 90 to 150 mM, 100 to 150 mM, 120 to 150 mM, 150 to 180 or 150 to 170 mM, and most preferably the concentration is 150 mM.

In a most preferred embodiment the inorganic salt is NaCl with a concentration of 150 mM.

In a further embodiment the pharmaceutical composition comprises an inorganic salt, preferably NaCl, preferably in a concentration of 150 mM, polysorbate 20 in a concentration of 0.01% (w/v), and a Histidine hydrochloride/L-histidine buffer with a concentration of 10 mM and a pH of 5.5, or a Histidine hydrochloride/L-histidine buffer with concentration of 10 mM and a pH of 6.2, or a $Na_2HPO_4/NaH_2PO_4$ buffer with concentration of 10 mM and a pH of 6.2, or a $Na_2HPO_4/NaH_2PO_4$ buffer with concentration of 10 mM and a pH of 6.5.

The term "antibody" or "immunoglobulin" is used herein in the broadest sense and includes full length antibodies, genetically engineered antibodies, recombinant antibodies, multivalent antibodies, monoclonal antibodies, polyclonal antibodies, bispecific antibodies, multispecific antibodies, chimeric antibodies, humanized antibodies, fully human antibodies, as well as fragments of such antibodies as long as they remain functional and exhibit the desired biological activity. The "Biological activity" of an antibody refers to the ability of the antibody to bind to antigen and result in a biological response which can be measured in vitro or in vivo.

A full length antibody comprises an antigen-binding variable region of the light ($V_L$) and heavy chain ($V_H$), a light chain constant region ($C_L$) and heavy chain constant domains $C_H1$, $C_H2$ and $C_H3$.

The term "antibody fragment" or "antigen-binding fragment" is used herein in the broadest sense and comprises a portion of a full length antibody, preferably comprising the antigen-binding or variable region thereof. An antibody fragment retains the original specificity of the parent immunoglobulin. Examples of antibody fragments include, e.g., Fab, Fab', F(ab')$_2$, and Fv fragments, diabodies, linear antibodies, single-chain antibody molecules, and multispecific antibodies formed from antibody fragment(s). Preferably, the antibody fragment is a Fab fragment.

A "monoclonal antibody" is an antibody that is specific for a single epitope of an antigen, i.e. directed against a single determinant on an antigen. Methods for producing monoclonal antibodies are known to the person skilled in the art.

The term "recombinant antibody" refers to all antibodies prepared, expressed, created or isolated by recombinant means, such as antibodies isolated from a transgenic host cell, such as e.g. a NS0 or CHO cell, or from an animal transgenic for immunoglobulin genes, or antibodies expressed using recombinant expression vectors transfected into a host cell, such as e.g. SP 2/0 mouse myeloma cells.

A "humanised antibody" is a human antibody wherein the antigen binding portion (CDR) is derived from non-human species, such as a mouse, and thus has a different specificity compared to the parent immunoglobulin. The CDR protein sequences can be modified to increase their similarities to antibody variants produced naturally in humans.

The term "anti-VEGF antibody" refers to an antibody that specifically binds to VEGF and inhibits one or more of its biological activities, e.g. its mitogenic, angiogenic and/or vascular permeability activity. Anti-VEGF antibodies act, e.g., by interfering with the binding of VEGF to a cellular receptor, by interfering with vascular endothelial cell activation after VEGF binding to a cellular receptor, or by killing cells activated by VEGF. Anti-VEGF antibodies include, e.g., antibodies A4.6.1, bevacizumab, ranibizumab, G6, B20, 2C3, and others as described in, for example, WO 98/45331, US 2003/0190317, U.S. Pat. No. 6,582,959, U.S. Pat. No. 6,703,020, WO 98/45332, WO 96/30046, WO 94/10202, WO 2005/044853, EP 0 666 868 B1, and Popkov et al., J Immunol Meth, 2004, 288:149-64. Preferably, the anti-VEGF antibody or antigen-binding fragment thereof present in the pharmaceutical composition of the present invention is ranibizumab or bevacizumab. Most preferably, it is ranibizumab.

"Ranibizumab" is a humanised monoclonal Fab fragment directed against VEGF-A having the light and heavy chain variable domain sequences of Y0317 as described in SEQ ID Nos. 115 and 116 of WO 98/45331 and Chen et al., J Mol Biol, 1999, 293:865-81. The CAS number of ranibizumab is 347396-82-1. Ranibizumab inhibits endothelial cell proliferation and neovascularisation and has been approved for the treatment of neovascular (wet) age-related macular degeneration (AMD), the treatment of visual impairment due to diabetic macular oedema (DME), the treatment of visual impairment due to macular oedema secondary to retinal vein occlusion (branch RVO or central RVO), or treatment of visual impairment due to choroidal neovascularisation (CNV) secondary to pathologic myopia.

Ranibizumab is related to bevacizumab and derived from the same parent mouse antibody as bevacizumab but it is much smaller than the parent molecule and has been affinity matured to provide stronger binding to VEGF-A. Ranibizumab is produced recombinantly in *Escherichia coli*, e.g. as described in WO 9845331 A2. The present commercial ranibizumab formulation contains α,α-trehalose dihydrate, histidine hydrochloride monohydrate, histidine, polysorbate 20 and water for injection and is supplied in a concentration of 10 mg/ml.

"Bevacizumab" is a full-length, humanized murine monoclonal antibody that recognizes all isoforms of VEGF and which is the parent antibody of ranibizumab. The CAS number of bevacizumab is 216974-75-3. Bevacizumab inhibits angiogenesis and is presently approved for the treatment of different cancer types. However, it is also used off-label in ophthalmological diseases such as age-related macular degeneration. The present commercial bevacizumab formulation contains α,α-trehalose dihydrate, sodium phosphate, polysorbate 20 and water for injection and is supplied as a concentrate with a concentration of 25 mg/ml.

The antibody concentration in the pharmaceutical compositions of the present invention is typically 1-100 mg/ml, preferably 2-75 mg/ml, more preferably 3-50 mg/ml, even more preferably 5 to 30 mg/ml and most preferably 6 or 10 mg/ml.

The terms "saccharide" or "sugar" refer to an organic compound comprising only carbon, hydrogen, and oxygen, usually with a hydrogen:oxygen atom ratio of 2:1 and the empirical formula $C_m(H_2O)_n$. The term "saccharides" includes mono-, di-, oligo- and polysaccharides. Examples of saccharides include glucose, fructose, galactose, xylose, ribose, sucrose, mannose, lactose, maltose, trehalose, starch, and glycogen. Various other forms of sugars are known, e.g., sugar alcohols such as glycerol, mannitol, sorbitol, and xylitol; sugar acids, e.g. aldonic acids such as ascorbic acid, aldaric acids such as tartaric acid; reducing sugars, e.g. glucose, glyceraldehydes, galactose, lactose, and maltose; amino sugars, e.g. N-acetylglucosamine, galactosamine, glucosamine, and sialic acid; or sulfoquinovose, a sulphonic acid derivative of glucose. Pharmaceutical compositions of the present invention do not contain any saccharides.

A pharmaceutical composition which "does not contain saccharides" or "contains no saccharides" means a composition which does not contain any of the above saccharides or other saccharides falling within the above definition.

The pharmaceutical composition of the present invention may further contain diluents, solubilising agents, isotonising agents, excipients, pH-modifiers, soothing agents, buffers, sulphur-containing reducing agents, antioxidants or the like, as long as it does not contain saccharides.

Preferably, the pharmaceutical composition of the present invention contains histidine hydrochloride/L-histidine, polysorbate 20, NaCl, water and ranibizumab and no further components or active substances, i.e. the pharmaceutical composition consists of histidine hydrochloride/L-histidine, polysorbate 20, NaCl, water and ranibizumab. More preferably, the pharmaceutical composition of the present invention consists of 10 mM histidine hydrochloride/L-histidine, 0.01% (w/v) polysorbate 20, 150 mM NaCl, water and 10 mg/ml ranibizumab.

An "intraocular neovascular disease" is a disease characterized by ocular neovascularisation. Examples of intraocular neovascular diseases include, e.g., proliferative retinopathies, choroidal neovascularisation (CNV), age-related macular degeneration (AMD), diabetic and other ischemia-related retinopathies, diabetic macular oedema, pathological myopia, von Hippel-Lindau disease, histoplasmosis of the eye, Central Retinal Vein Occlusion (CRVO), Branch Retinal Vein Occlusion (BRVO), corneal neovascularisation, and retinal neovascularisation. The term "age-related macular degeneration" refers to a medical condition which usually affects older adults and results in a loss of vision in the centre of the visual field (the macula) because of damage to the retina.

The term "intravitreal injection" refers to the administration of a pharmaceutical composition in which the substance is injected directly into the eye. More specifically, the substance is injected into the vitreous humour (also called vitreous body or simply vitreous) which is the clear gel that fills the space between the lens and the retina of the eyeball of humans and other vertebrates.

Pharmaceutical compositions of the present invention can be supplied in sealed and sterilized plastic, glass or other suitable containers having a defined volume such as vials, ampoules or syringes or a large volume such as bottles. It is preferred that the liquid pharmaceutical composition containing an anti-VEGF antibody is supplied in a prefilled syringe. A "ready-to-use syringe" or "prefilled syringe" is a syringe which is supplied in a filled state, i.e. the pharmaceutical composition to be administered is already present in the syringe and ready for administration. Prefilled syringes have many benefits compared to separately provided syringe and vial, such as improved convenience, affordability, accuracy, sterility, and safety. The use of prefilled syringes results in greater dose precision, in a reduction of the potential for needle sticks injuries that can occur while drawing medication from vials, in pre-measured dosage reducing dosing errors due to the need to reconstituting and/or drawing medication into a syringe, and in less overfilling of the syringe helping to reduce costs by minimising drug waste.

In a preferred embodiment the pH of the liquid pharmaceutical composition of the present invention is in the range of 5.0 to 7.0, 5.1 to 6.9, 5.2 to 6.8, 5.3 to 6.7 or 5.4 to 6.6. In a more preferred embodiment the pH of the liquid pharmaceutical composition of the present invention is in the range of 5.5 to 6.5 or 5.5 to 6.2. Most preferably, the pH of the liquid pharmaceutical composition of the present invention is 5.5 or 6.2.

In another aspect, the invention concerns a liquid pharmaceutical composition for intravitreal administration comprising a buffer in a concentration of 5 to 250 mM, a non-ionic surfactant, an inorganic salt, and an anti-VEGF antibody or antigen-binding fragment thereof, wherein the composition does not contain saccharides.

In another aspect, the invention relates to a liquid pharmaceutical composition for intravitreal administration comprising histidine hydrochloride/L-histidine in a concentration of 5 to 250 mM, a non-ionic surfactant in a concentration of 0.005 to 0.02% (w/v), an inorganic salt, and an anti-VEGF antibody or antigen-binding fragment thereof, wherein the composition does not contain saccharides.

In a further embodiment the pharmaceutical composition in the absence of an inorganic salt comprises polysorbate, preferably polysorbate 20, most preferably polysorbate 20 in a concentration of 0.01% (w/v), and a histidine hydrochloride/L-histidine buffer with a concentration of 185 mM with pH 5.5, or 220 mM with pH 6.2, or 240 mM with pH 6.5. In a further embodiment the liquid pharmaceutical composition in the presence of an inorganic salt, such as NaCl, comprises polysorbate, preferably polysorbate 20, most preferably in a concentration of 0.01% (w/v), and a histidine hydrochloride/L-histidine buffer with a concentration of 10 mM and a pH of 5.5, or a histidine hydrochloride/L-histidine buffer with concentration of 10 mM and a pH of 6.2, or a $Na_2HPO_4/NaH_2PO_4$ buffer with concentration of 10 mM and a pH of 6.2, or a $Na_2HPO_4/NaH_2PO_4$ buffer with concentration of 10 mM and a pH of 6.5. Further preferred is that the inorganic salt is NaCl with a concentration of 150 mM and the buffer is histidine hydrochloride/L-histidine with a concentration of 10 mM and a pH of 5.5 or 6.2.

In another aspect, the invention relates to a liquid pharmaceutical composition for intravitreal administration comprising histidine hydrochloride/L-histidine in a concentration of 5 to 250 mM, polysorbate 20 in a concentration of 0.005 to 0.02% (w/v), an inorganic salt in a concentration of 10 to 200 mM, and an anti-VEGF antibody or antigen-binding fragment thereof, wherein the composition does not contain saccharides.

In another aspect, the invention concerns a liquid pharmaceutical composition for intravitreal administration comprising Histidine hydrochloride/L-histidine in a concentration of 5 to 250 mM, polysorbate 20 in a concentration of 0.005 to 0.02% (w/v), NaCl in a concentration of 10 to 200 mM, and an anti-VEGF antibody or antigen-binding fragment thereof in a concentration 10 mg/ml, wherein the composition does not contain saccharides.

In a preferred embodiment the anti-VEGF antibody or antigen-binding fragment thereof is a humanized monoclonal antibody or antigen-binding fragment. In a particular preferred embodiment the anti-VEGF antibody is an antigen-binding fragment, more preferably a Fab fragment. In another more preferred embodiment the anti-VEGF antibody is a humanized monoclonal Fab fragment. In the most preferred embodiment the anti-VEGF antibody is ranibizumab.

In a further embodiment the pharmaceutical composition in the absence of an inorganic salt comprises ranibizumab, polysorbate 20 in a concentration of 0.01% (w/v), and a histidine hydrochloride/L-histidine buffer with a concentration of 185 mM with pH 5.5, or 220 mM with pH 6.2, or 240 mM with pH 6.5. In a further embodiment the liquid pharmaceutical composition comprises ranibizumab, 150 mM NaCl, polysorbate 20 in a concentration of 0.01% (w/v), and a histidine hydrochloride/L-histidine buffer with a concentration of 10 mM and a pH of 5.5, or a histidine hydrochloride/L-histidine buffer with concentration of 10 mM and a pH of 6.2, or a $Na_2HPO_4/NaH_2PO_4$ buffer with concentration of 10 mM and a pH of 6.2, or a $Na_2HPO_4/NaH_2PO_4$ buffer with concentration of 10 mM and a pH of 6.5.

In another aspect, the invention concerns a liquid pharmaceutical composition for intravitreal administration comprising histidine hydrochloride/L-histidine in a concentration of 5 to 250 mM, polysorbate 20 in a concentration of 0.005 to 0.02%, NaCl in a concentration of 10 to 200 mM, and ranibizumab, wherein the composition does not contain saccharides. In another embodiment the pharmaceutical composition of the invention consists of said components and does not contain any further components or active substances.

In a further aspect, the invention concerns a liquid pharmaceutical composition for intravitreal administration comprising histidine hydrochloride/L-histidine in a concentration of 10 mM, polysorbate 20 in a concentration of 0.005 to 0.02% (w/v), NaCl in a concentration of 10 to 200 mM, and ranibizumab, wherein the composition does not contain saccharides. In another embodiment the pharmaceutical composition of the invention consists of said components and does not contain any further components or active substances.

In a further aspect, the invention concerns a liquid pharmaceutical composition for intravitreal administration comprising histidine hydrochloride/L-histidine in a concentration of 10 mM, polysorbate 20 in a concentration of 0.01%, NaCl in a concentration of 10 to 200 mM, and ranibizumab, wherein the composition does not contain saccharides. In another embodiment the pharmaceutical composition of the invention consists of said components and does not contain any further components or active substances.

In a further aspect, the invention concerns a liquid pharmaceutical composition for intravitreal administration comprising histidine hydrochloride/L-histidine in a concentration of 10-20 mM, polysorbate 20 in a concentration of 0.01% (w/v), NaCl in a concentration of 150 mM, and ranibizumab, wherein the composition does not contain saccharides. In another embodiment the pharmaceutical composition of the invention consists of said components and does not contain any further components or active substances.

In a further aspect, the invention concerns a liquid pharmaceutical composition for intravitreal administration comprising histidine hydrochloride/L-histidine in a concentration of 10-20 mM, polysorbate 20 in a concentration of 0.005 to 0 0.015% (w/v), NaCl in a concentration of 150 mM, and ranibizumab, wherein the composition does not contain saccharides. In another embodiment the pharmaceutical composition of the invention consists of said components and does not contain any further components or active substances.

In a further aspect, the invention concerns a liquid pharmaceutical composition for intravitreal administration comprising histidine hydrochloride/L-histidine in a concentration of 10-20 mM, polysorbate 20 in a concentration of 0.005 to 0 0.015% (w/v), NaCl in a concentration of 125 to 175 mM, and ranibizumab, wherein the composition does not contain saccharides. In another embodiment the pharmaceutical composition of the invention consists of said components and does not contain any further components or active substances.

In another aspect, the invention concerns a liquid pharmaceutical composition for intravitreal administration comprising $Na_2HPO_4/NaH_2PO_4$ in a concentration of 5 to 100 mM, polysorbate 20 in a concentration of 0.005 to 0.02% (w/v), NaCl in a concentration of 10 to 200 mM, and ranibizumab, wherein the composition does not contain saccharides. In another embodiment the pharmaceutical composition of the invention consists of said components and does not contain any further components or active substances.

A preferred embodiment of the invention is a liquid pharmaceutical composition for intravitreal administration comprising 10 mM histidine hydrochloride/L-histidine, 0.01% (w/v) polysorbate 20, 150 mM NaCl, and ranibizumab, wherein the composition does not contain saccharides. In another embodiment the pharmaceutical composition of the invention consists of said components and does not contain any further components or active substances.

In another embodiment, the invention concerns a liquid pharmaceutical composition for intravitreal administration comprising 10 mM $Na_2HPO_4/NaH_2PO_4$, 0.01% (w/v) polysorbate 20, 150 mM NaCl, and ranibizumab, wherein the composition does not contain saccharides. In another embodiment the pharmaceutical composition of the invention consists of said components and does not contain any further components or active substances.

Another preferred embodiment of the invention is a liquid pharmaceutical composition for intravitreal administration consisting of a histidine-containing buffer in a concentration of 5 to 250 mM, a non-ionic surfactant in a concentration of 0.005 to 0.02% (w/v), an inorganic salt in a concentration of 10 to 200 mM, and an anti-VEGF antibody in a concentration of 1 to 100 mg/ml.

Another particularly preferred embodiment of the invention is a liquid pharmaceutical composition for intravitreal administration consisting of Histidine hydrochloride/L-histidine in a concentration of 5 to 250 mM, polysorbate 20 in a concentration of 0.005 to 0.02% (w/v), NaCl in a concentration of 10 to 200 mM, and ranibizumab in a concentration of 1 to 100 mg/ml.

The liquid pharmaceutical composition of the present invention may be used in the treatment of an intraocular neovascular disease such as age-related macular degeneration (AMD), in the treatment of visual impairment due to diabetic macular oedema (DME), in the treatment of visual impairment due to macular oedema secondary to retinal vein occlusion (branch RVO or central RVO), or in the treatment of visual impairment due to choroidal neovascularisation (CNV) secondary to pathologic myopia.

In particular, the invention relates to a liquid pharmaceutical composition for use in the treatment of an intraocular neovascular disease such as AMD comprising a buffer, a non-ionic surfactant, an inorganic salt and an anti-VEGF antibody, wherein the composition does not contain saccharides.

In a preferred embodiment of the invention the liquid pharmaceutical composition for intravitreal administration for use in the treatment of an intraocular neovascular disease such as AMD comprises a buffer in a concentration of 5 to 250 mM, a non-ionic surfactant in a concentration of 0.005 to 0.02% (w/v), an inorganic salt in a concentration of 10 to 200 mM and an anti-VEGF antibody, wherein the composition does not contain saccharides.

In another preferred embodiment of the invention the liquid pharmaceutical composition for intravitreal administration for use in the treatment of an intraocular neovascular disease such as AMD comprises histidine hydrochloride/L-histidine in a concentration of 5 to 250 mM, polysorbate 20 in a concentration of 0.005 to 0.02% (w/v), NaCl in a concentration of 10 to 200 mM, and ranibizumab, wherein the composition does not contain saccharides.

In another preferred embodiment of the invention the liquid pharmaceutical composition for intravitreal administration for use in the treatment of an intraocular neovascular disease such as AMD comprises 10 mM histidine hydrochloride/L-histidine, 0.01% (w/v) polysorbate 20, 150 mM NaCl, and ranibizumab, wherein the composition does not contain saccharides.

In a further preferred embodiment of the invention the liquid pharmaceutical composition for intravitreal administration for use in the treatment of an intraocular neovascular disease such as AMD consists of 10 mM Histidine hydrochloride/L-histidine, 0.01% (w/v) polysorbate 20, 150 mM NaCl, and ranibizumab.

Moreover, the invention encompasses the intravitreal administration of the liquid pharmaceutical composition of the invention to a subject in an effective amount to treat an intraocular neovascular disease such as AMD. In a preferred embodiment, the liquid pharmaceutical composition of the invention for intravitreal administration is present in a prefilled syringe.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

The detailed description is merely exemplary in nature and is not intended to limit application and uses. The following examples further illustrate the present invention without, however, limiting the scope of the invention thereto. Various changes and modifications can be made by those skilled in the art on the basis of the description of the invention, and such changes and modifications are also included in the present invention.

EXAMPLES

Example 1

Preparation of Samples

Different formulations of ranibizumab were prepared according to Table 1.

TABLE 1

Pharmaceutical compositions tested. Of these samples, V1 corresponds to the commercially available ranibizumab (Lucentis ®) formulation.

| Sample | pH | buffer | osmoregulator | surface-active substance |
|---|---|---|---|---|
| V1 | 5.5 | 10 mM L-His/His-HCl | 10% Trehalose | 0.01% (w/v) polysorbate 20 |
| V2 | 5.5 | 10 mM L-His/His-HCl | 150 mM NaCl | |
| V3 | 5.5 | 185 mM L-His/His-HCl | — | |
| V4 | 6.2 | 10 mM L-His/His-HCl | 150 mM NaCl | |
| V5 | 6.2 | 220 mM L-His/His-HCl | — | |
| V6 | 6.2 | 10 mM $Na_2HPO_4$/$NaH_2PO_4$ | 150 mM NaCl | |
| V7 | 6.5 | 240 mM L-His/His-HCl | — | |
| V8 | 6.5 | 10 mM $Na_2HPO_4$/$NaH_2PO_4$ | 150 mM NaCl | |

To reach isotonicity the buffers containing only L-His/His-HCl as osmoactive substance had to be adjusted to 300 mOsmol/kg +/−20 mOsmol/kg by increasing the buffer concentration.

The pharmaceutical compositions were prepared without ranibizumab which was dialysed into them afterwards.

Preparation of L-Histidine Containing Formulations:

| Sample | pH | L-Histidine (g) | L-Histidine HCl (g) | Osmoregulator [g] | Polysorbate 20 [µL] |
|---|---|---|---|---|---|
| V1 | 5.5 | 0.226 | 1.162 | 70 g trehalose | 70 |
| V2 | 5.5 | 0.226 | 1.162 | 6,136 g NaCl | 70 |
| V3 | 5.5 | 4.524 | 23.236 | — | 70 |
| V4 | 6.2 | 0.618 | 0.633 | 6,136 g NaCl | 70 |
| V5 | 6.2 | 13.587 | 13.926 | — | 70 |
| V7 | 6.5 | 18.886 | 9.701 | 6,136 g NaCl | 70 |

The listed amounts of L-Histidine, L-Histidine HCl and the osmoregulator (Trehalose/NaCl) were dissolved in 500 mL water. 70 µl Polysorbate 20 was added. The volume was filled with water to 700 mL. The ratio of basic and acidic L-Histidine led to the indicated pH. The osmolality was determined by Gonotec Osmomat 030.

Preparation of Phosphate Containing Formulations:

For the preparation of the phosphate containing buffer system 10 mM solutions of di-sodium hydrogen phosphate and sodium dihydrogen phosphate were prepared:
10 mM $Na_2HPO_4$*2 $H_2O$ 3.56 g $Na_2HPO_4$*2 $H_2O$ were weight and solved in 1800 mL $H_2O$. The volume was filled to 2000 mL with $H_2O$.
10 mM $NaH_2PO_4$*2 $H_2O$ 3.12 g $NaH_2PO_4$*2 $H_2O$ were weight and solved in 1800 ml $H_2O$: The volume was filled to 2000 mL with $H_2O$.

| Sample number | pH | $Na_2HPO_4$ [g] | $NaH_2PO_4$ [g] | osmoregulator [g] | Polysorbate 20 [µL] |
|---|---|---|---|---|---|
| V6 | 6.2 | 130 | 570 | 6.136 g NaCl | 70 |
| V8 | 6.5 | 220 | 480 | 6.136 g NaCl | |

Sodium chloride and Polysorbate 20 were dissolved in the indicated amounts of $Na_2HPO_4$ and $NaH_2PO_4$ in 700 mL water. The ratio of basic and acidic components of the buffer led to a pH of 6.2 respectively 6.5. The osmolality was determined by Gonotec Osmomat 030.

Before dialysis the tubes were hydrated with $H_2O$ and five vials of ranibizumab were pooled to assure comparable starting conditions for all tested formulations. Ranibizumab was diluted with the corresponding new formulation system to a concentration of 3 mg/ml. The samples were dialyzed overnight. After removing the samples quantitatively from the dialysis tubes the concentration was determined by UV at 280 nm. After UV measurement the samples were further diluted to 1 mg/ml with the corresponding buffer. After sterile filtration each formulation was filled into sterile 2R vials and frozen at −80° C.

For differential scanning fluorometry (DSF) (see below) measurements 10 µl of each formulation were taken after sterile filtration and filling into sterile 2R vials and tested without being frozen.

Example 2

Stress Conditions

To obtain the best fitting formulation conditions the samples were analyzed after subjecting them to different stress conditions. These stress conditions were chosen to force the chemical and physical degradation pathways of ranibizumab and included the following conditions:

a) 40° C. storage (samples were stored at 40° C. and 75% relative humidity for 14 d and 28 d), b) shaking (samples were shaken with 300 rpm at 25° C. for 7 d), and c) freeze/thaw (samples were frozen and thawed four times (5° C. to −20° C.) with a rate of ±1° C./min; after each cooling/heating step the temperature (5° C. and −20° C. respectively) was kept constant for 10 minutes).

After the samples were subjected to the different stress conditions, aliquots were taken and subjected to analysis, e.g. by differential scanning fluorometry (DSF), isoelectric focusing (IEF), sodium dodecylsulphate polyacrylamide gel electrophoresis (SDS-PAGE), reversed phase high performance liquid chromatography (RP-HPLC), and asymmetric flow field-flow fractionation (AF4).

Example 3

Analysis by Differential Scanning Fluorometry

The temperature at which the protein unfolds was determined by an increase in the fluorescence of a dye with affinity for hydrophobic parts of the protein which are exposed as the protein unfolds. The stabilizing effect of the formulation on the physical stability of the protein is supposed to be higher, if the melting point is higher.

Samples were diluted to 0.1 mg/ml containing 10× sypro orange and measured using a Real Time Q-PCR Cycler CFX96 (BioRad). A temperature ramp from 25° C. to 95° C. with 1° C. increments and 30 s holding time was performed. The HEX channel was chosen for fluorescence measurements.

The results of the DSF analysis are summarised in Table 2. Only sample V3 showed a significantly lower melting point of 70° C. compared to the other formulations. This measurement was successfully reproduced. All other formulations did not clearly differ in their ranibizumab melting point.

TABLE 2

DSF Analysis of different formulations.

| Sample | pH | buffer | osmoregulator | Melting point [° C.] |
|---|---|---|---|---|
| Lucentis ® | 5.5 | 10 mM L-His/His-HCl | 10% Trehalose | 74 |
| V1 | 5.5 | 10 mM L-His/His-HCl | 10% Trehalose | 74 |
| V2 | 5.5 | 10 mM L-His/His-HCl | 150 mM NaCl | 73 |
| V3 | 5.5 | 185 mM L-His/His-HCl | — | 70 |
| V4 | 6.2 | 10 mM L-His/His-HCl | 150 mM NaCl | 74 |
| V5 | 6.2 | 220 mM L-His/His-HCl | — | 73 |
| V6 | 6.2 | 10 mM Na$_2$HPO$_4$/NaH$_2$PO$_4$ | 150 mM NaCl | 74 |
| V7 | 6.5 | 240 mM L-His/His-HCl | — | 74 |
| V8 | 6.5 | 10 mM Na$_2$HPO$_4$/NaH$_2$PO$_4$ | 150 mM NaCl | 74 |

Example 4

Isoelectric Focusing

Isoelectric focusing (IEF) is a technique for separating different molecules by differences in their isoelectric point (pI). This analytical method is used to determine chemical modifications of ranibizumab like deamidation that lead to a change of the molecule charge.

Experiments were performed using Focus gels pH 6-11, size 250×115×0.65 mm (Serva), horizontal gel electrophoresis hardware Multiphor II (GE Healthcare Bio-Sciences), power supply EPS 3500 XL (GE Healthcare Bio-Sciences) and cooling plate (Lauda RE 104). Samples were diluted to 0.5 mg/ml with water and 5 μg were plotted on the anode side of the gel (n=2). The IEF run was performed at 5° C. Afterwards the gel was washed with water and dyed with Coomassie overnight. After discoloration for at least 5 h the gel was scanned and analyzed using QuantityOne Software. The run conditions are shown in the following table:

TABLE 3

Conditions for IEF run

| phase | time [min] | power [W] | current [mA] | voltage [V] |
|---|---|---|---|---|
| pre-focusing | 20 | 5 | 25 | 1000 |
| sample diffusion | 30 | 10 | 30 | 500 |
| focusing | 90 | 20 | 18 | 1500 |
| band sharpening | 30 | 24 | 14 | 2000 |

Figure 1:
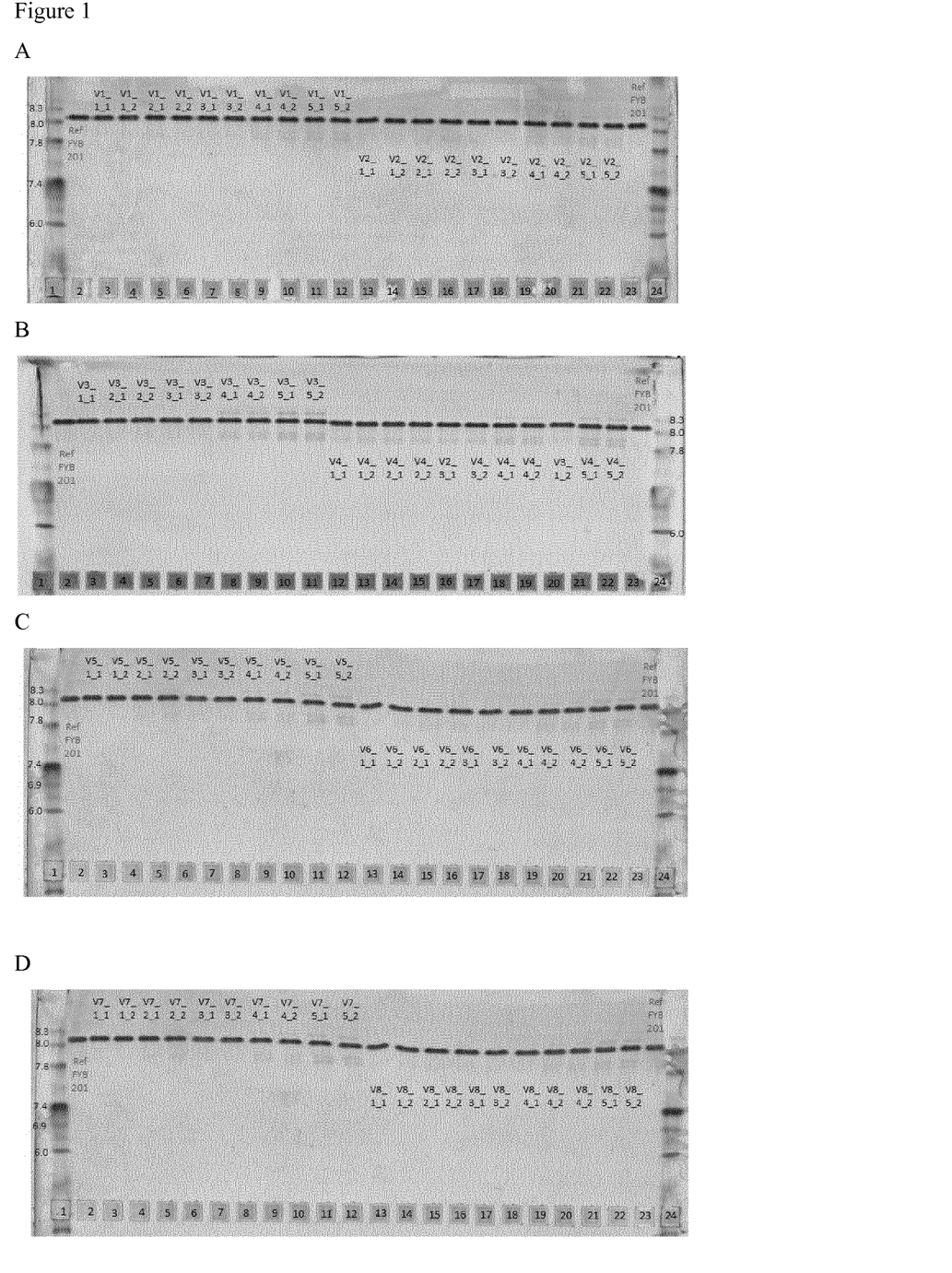
FIG. 1. Results from the isoelectric focusing (IEF). Each sample was analysed in duplicate. 1: dialyzed, 2: shaking, 3: freeze/thaw, 4: 40° C. for 14 d, 5: 40° C. for 28 d. Lane 1 and 24: marker; lane 2 and 23: ranibizumab (reference). A) Samples V1 (lanes 3-12) and V2 (lanes 13-22), B) Samples V3 (lanes 3-12) and V4 (lanes 13-22), C) Samples V5 (lanes 3-12) and V6 (lanes 13-22), D) Samples V7 (lanes 3-12) and V8 (lanes 13-22).

The gels are shown in FIG. 1. All samples showed a main band at a pI slightly above 8.0. Furthermore all samples including dialysed reference sample V1 showed two additional slight bands below the main band after storage at 40° C. These bands were least intense for V2 and most intense in V3 and V4 where an additional band above the main band was present as well. However, it has to be noted that the gel of samples V3 and V4 seems to be not as discoloured as the others (see sample application slots). Between samples V5-V8 no significant differences were observed.

Example 5

SDS PAGE

By SDS-PAGE physical modifications like fragmentation and oligomerisation of ranibizumab in the different formulations were determined.

The SDS-PAGE was performed under reducing conditions. Samples were diluted to 0.4 mg/ml with water and further diluted to 0.2 mg/ml with reducing SDS sample buffer. The samples were incubated at 95° C. for 5 min. The sample wells were washed with running buffer prior to application of the samples (n=2). After the run the gel was washed with water and dyed with Coomassie overnight. After discoloration the gel was scanned and analyzed using QuantityOne Software.

The running conditions were as follows:
voltage: 250 V
current: 50 mA/gel
power: 12.5 W
time: 40 min In SDS-PAGE all samples showed twobands under the reducing conditions: band 1 was approximately at about 27.5 kDa and band 2 at about 26.5 kDa. The results were the same after subjecting the samples to different stress conditions and there were no differences between the different tested sample compositions and the original ranibizumab formulation.

Example 6

Asymmetrical Flow Field-Flow Fractionation

By Asymmetrical flow field-flow fractionation (AF4) molecules can be separated and characterized according to their molecular weight because of their differing diffusion coefficients. Hence, physical modifications of ranibizumab like aggregation are determined.

Samples were diluted to 0.3 mg/ml with ranibizumab formulation buffer (without polysorbate 20) and measured in duplicates (30 μg per injection). A MALS detector gives information about the molecular size distribution of the sample and a UV detector allows quantification.

Figure 2:
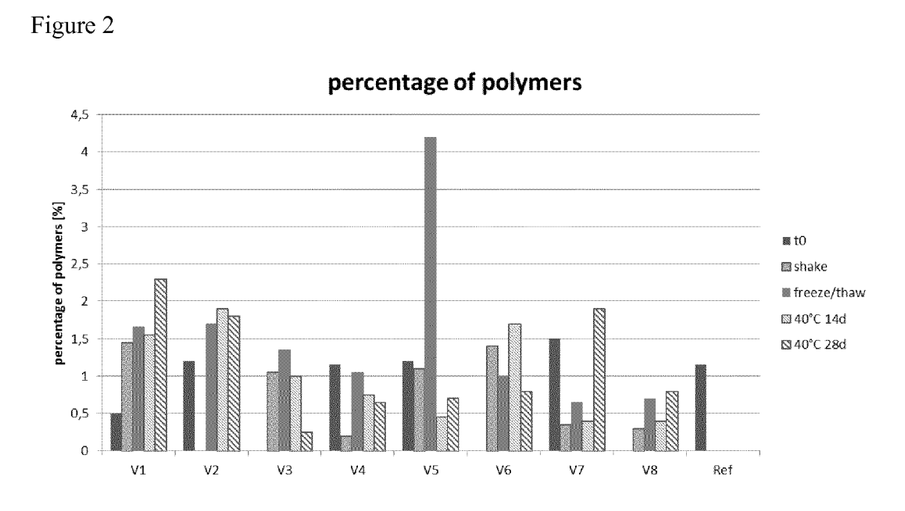
FIG. 2. Percentage of polymers in the different formulations V1 to V8 and the reference Lucentis® formulation subjected to different stress conditions. Mean from two measurements.

The mean percentages of polymers are displayed in FIG. 2 and show that there are no significant differences between the formulations except for sample V5 after freeze/thaw (where only one of two runs was evaluated). Between 0% and 2% aggregates are present in the formulations and the amount does not increase during the performed stress tests.

Example 7

Determination of Protein Concentration by RP-HPLC

RP-HPLC allows protein characterization and quantification by hydrophobic interaction of ranibizumab with the non-polar stationary phase and an aqueous, moderately polar mobile phase. By the use of an external calibration this method allows the quantification of unknown ranibizumab containing samples.

Samples were diluted to 0.03 mg/ml and 1.5 μg were injected (n=2). The measurement parameters are as follows:

| | |
|---|---|
| Column | YMC-Pack ODS-A |
| Column temperature | 70° C. |
| Auto sampler temperature | 8° C. |
| Injection volume | 50 µl |
| Flow rate | 0.8 ml/min |
| Detection | 280 nm and 214 nm |
| Run time | 15 min |

| | time [min] | eluent B [%] |
|---|---|---|
| Gradient | 0.0 | 25 |
| | 2.0 | 25 |
| | 7.0 | 85 |
| | 7.5 | 100 |
| | 8.0 | 100 |
| | 9.0 | 25 |
| | 15.0 | 25 |

Figure 3:
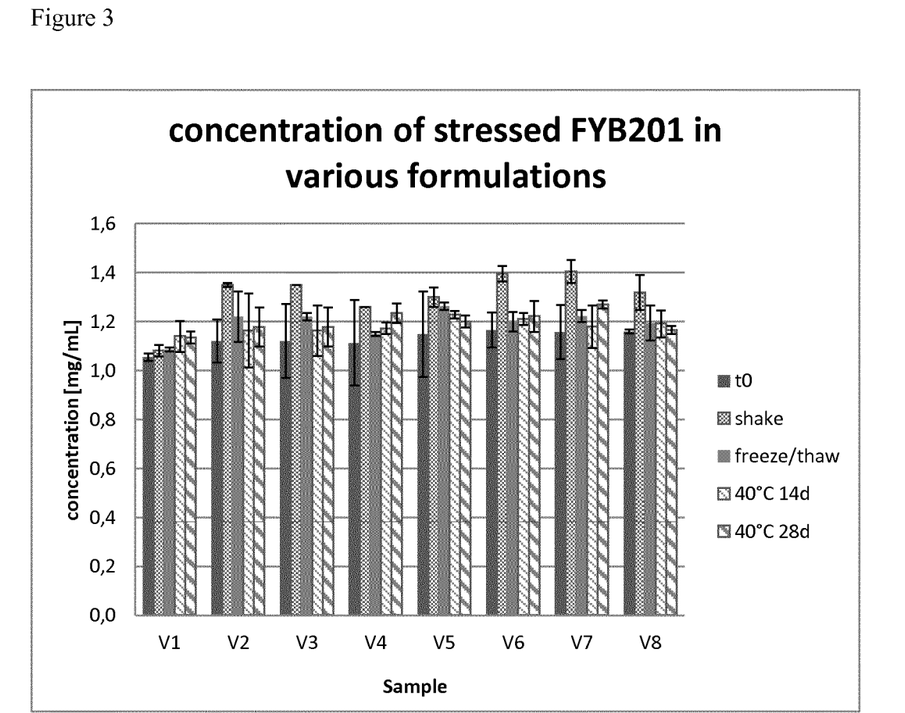
FIG. 3. Results of RP-HPLC quantity analysis. For each sample (V1 to V8) the bars represent the following treatments: dialysed (bar 1), shaken (bar 2), frozen/thawed (bar 3), storage at 40° C. for 14 d (bar 4) or storage at 40° C. for 28 d (bar 5).

The ranibizumab concentration was determined for all samples following dialysis (1), and after different stress tests described above, i.e. after shaking (2), freeze/thaw (3), 40° C. for 14 d (4), and 40° C. for 28 d (5). FIG. 3 shows that there were no significant differences between the formulations.

Example 8

Determination of Chemical Modifications by RP-HPLC

The ranibizumab containing formulations were further characterized regarding chemical modifications that lead to a shift in hydrophobicity like oxidation using a different RP-HPLC method.

Samples were measured undiluted and 10 µg were injected (n=2). The measurement parameters are as follows:

| | |
|---|---|
| Column | ZORBAX 300SB-C18 |
| Eluent A | 0.1% TFA in $H_2O$ |
| Eluent B | 0.1% TFA in 20% 1-propanol, 70% acetonitrile, 10% $H_2O$ |
| Column temperature | 65° C. |
| Auto sampler temperature | 8° C. |
| Injection volume | 10 µl |
| Flow rate | 1.0 ml/min |
| Detection | 280 nm and 214 nm |
| Run time | 45 min |

| | time [min] | eluent B [%] |
|---|---|---|
| Gradient | 0.0 | 0.0 |
| | 7.0 | 37.5 |
| | 10.0 | 37.5 |
| | 26.0 | 41.5 |
| | 31.0 | 41.5 |
| | 33.0 | 100.0 |
| | 35.0 | 100.0 |
| | 37.0 | 0.0 |
| | 45.0 | 0.0 |

Figure 4:
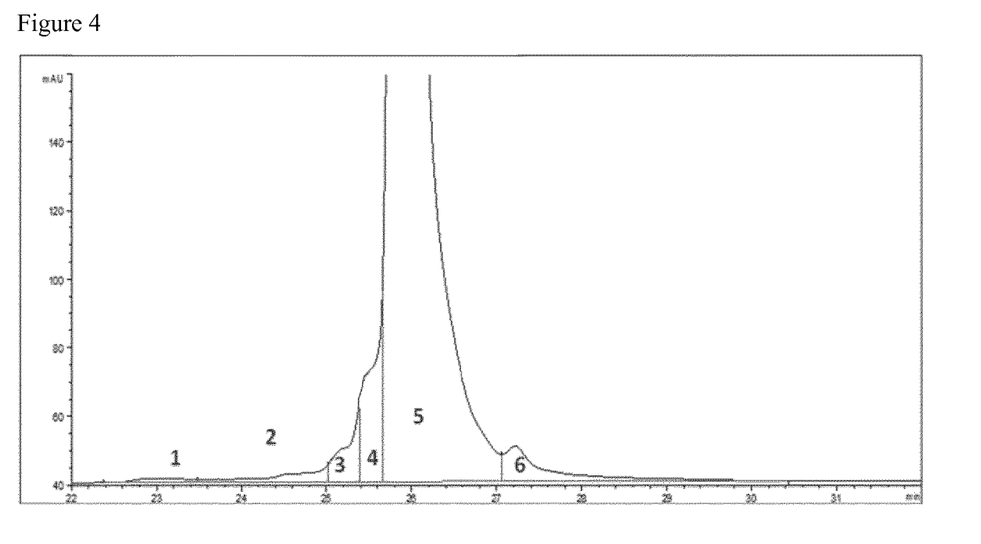
FIG. 4. Analysis of purity by RP-HPLC. Peak pattern of dialysed sample V1 (unstressed).

The peak pattern of dialysed reference sample V1 was determined and is shown in FIG. 4. Then, in the different formulations V2 to V8 the area changes of the peaks were investigated and compared to the peak pattern of dialysed reference sample V1.

To compare the samples the absolute change of the relative areas was determined and the purity was calculated by the following formula:

Δrel. area=rel. area of peakx in sample y−rel. area of peakx in dialysed V1

Figure 5:
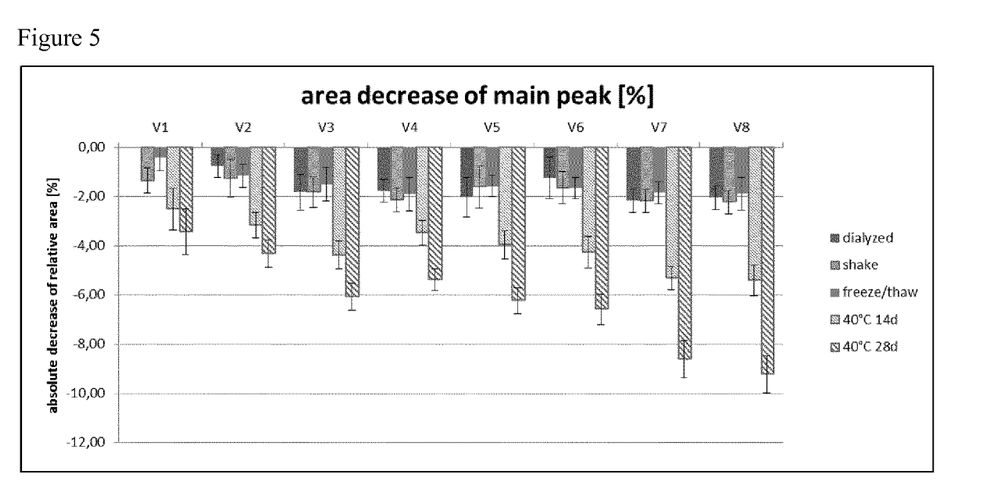
FIG. 5. Analysis of purity by RP-HPLC. Area decrease of the main peak (peak 5) as indicated in FIG. 4. For each sample (V1 to V8) the bars represent the following treatments: dialysed (bar 1), shaken (bar 2), frozen/thawed (bar 3), storage at 40° C. for 14 d (bar 4) or storage at 40° C. for 28 d (bar 5).

The results for the decrease of the main peak area for all eight formulations and the different stress conditions are summarized in FIG. 5. The shown deviations are calculated as follows:

$SD_{total}$=$SD_{rel.\ area\ dialysed\ V1}$+$SD_{rel.\ area\ sample\ y}$

FIG. 5 shows the decrease of the relative main peak area. For the main peak (peak 5) shaking and freeze/thaw stress tests did not lead to a significant decrease of the main peak area whereas storage at 40° C. induced a decrease between 2.5% and 9.2% in all formulations. The formulations with pH 6.5 (V7, V8) showed the highest decrease, i.e. a higher pH seems to result in a stronger decrease of the main peak area. V2 was most similar to the comparative formulation V1.

In summary, only the storage at 40° C. led to significant changes in the peak pattern.

The relative main peak in the comparative formulation V1 decreased by 3.5%. V2 showed the most comparable results with a decrease of 4.3% followed by V4 (5.4% decrease). The reduction of the main peak was pH dependent as the formulations V7 and V8 with pH of 6.5 showed the highest increases with 8.6% and 9.2%, respectively.

In summary the differences between the tested formulations were just slightly distinct. Considering the RP HPLC purity results a pH of 5.5 seems to be optimal, but can be raised to pH 6.2 and the L-Histidine/Histidine-HCl buffer is more suitable than sodium phosphate.

The invention claimed is:

1. A liquid pharmaceutical composition for intravitreal injection comprising
   a) a histidine hydrochloride/L-histidine buffer,
   b) a non-ionic surfactant,
   c) 3-50 mg/ml of ranibizumab, and
   d) 50 to 170 mM of an inorganic salt which is NaCl,
   wherein the composition does not contain saccharides and wherein the pH of the composition is 5.5.

2. The pharmaceutical composition of claim 1, wherein the histidine hydrochloride/L-histidine buffer is present in a concentration of from 5 mM to 250 mM.

3. The pharmaceutical composition of claim 1, wherein the histidine hydrochloride/L-histidine buffer has a concentration of 10 mM.

4. The pharmaceutical composition of claim 1, wherein the non-ionic surfactant is polysorbate 20.

5. The pharmaceutical composition of claim 1, wherein the non-ionic surfactant is present in a concentration of from 0.002 to 0.02% (w/v).

6. A method of treating an intraocular neovascular disease in a patient in need thereof comprising administering the pharmaceutical composition of claim 1.

7. A prefilled syringe containing the pharmaceutical composition of claim 1.

8. The pharmaceutical composition of claim 1, wherein the inorganic salt is present in a concentration of 150 mM.

9. A liquid pharmaceutical composition for intravitreal injection consisting of 10 mM histidine hydrochloride/L-histidine, 0.01% polysorbate 20, 150 mM NaCl, 10 mg/ml ranibizumab and water with a pH of 5.5 or 6.2.

10. A method of treating an intraocular neovascular disease in a patient in need thereof comprising administering the pharmaceutical composition of claim 9.

11. A prefilled syringe containing the pharmaceutical composition of claim 9.

* * * * *